United States Patent [19]

Viesturs

[11] Patent Number: 4,794,935
[45] Date of Patent: Jan. 3, 1989

[54] INSTRUMENT FOR MEASURING PRESSURE

[75] Inventor: Eric Viesturs, Southbury, Conn.

[73] Assignee: Connecticut Artcraft Corp., Naugatuck, Conn.

[21] Appl. No.: 88,403

[22] Filed: Aug. 24, 1987

[51] Int. Cl.⁴ ............................................... A61B 5/10
[52] U.S. Cl. ........................................ 128/774; 73/172
[58] Field of Search ............................ 73/172; 128/774

[56] References Cited

U.S. PATENT DOCUMENTS

| | | | |
|---|---|---|---|
| 2,644,332 | 7/1953 | Ulrich | 73/172 |
| 3,513,698 | 5/1970 | Ross | 73/172 |
| 4,122,837 | 10/1978 | Leonard | 128/774 |
| 4,592,371 | 6/1986 | Pellicano et al. | 128/774 |

*Primary Examiner*—Lloyd L. King

[57] ABSTRACT

An instrument for measuring the pressure exerted upon a portion of the body of a bedridden individual lying on a mattress by that section of the mattress which is engaged by this body portion. A small flexible hollow member has a first air inlet and is adapted to be positioned for use between the body portion and the mattress section. A switch is disposed in the member with connecting leads extending out of the member. The switch is open when the air pressure in the member is at least equal to the exerted pressure and is closed when the air pressure in the member is less than the exerted pressure. A circuit including a lamp and an electric power source is connected to the switch to cause the lamp to be energized and lit when the switch is closed, the lamp being deenergized and dark when the switch is open. An air pressure meter has a second air inlet. A manually operated air pump is connected to both air inlets. When the member is positioned for use with the switch closed and the lamp energized, the pump is actuated and the pressure in the member is increased until the lamp is deenergized. The meter at the instant the lamp is deenergized displays the exerted pressure.

5 Claims, 3 Drawing Sheets

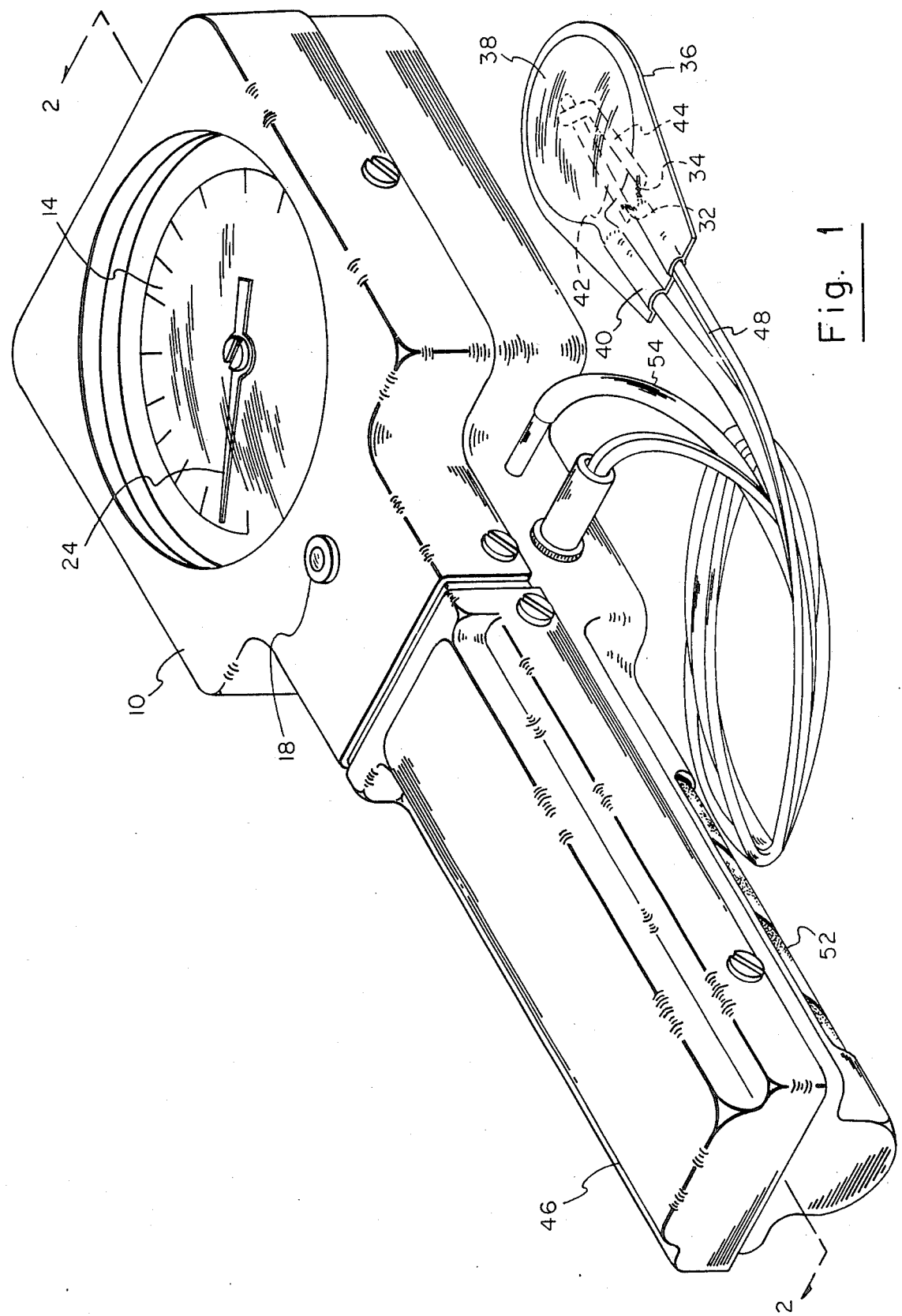

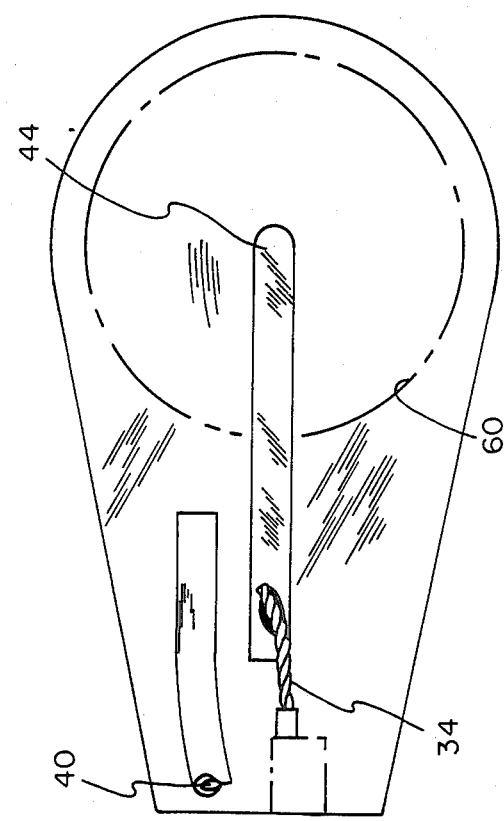
Fig. 5
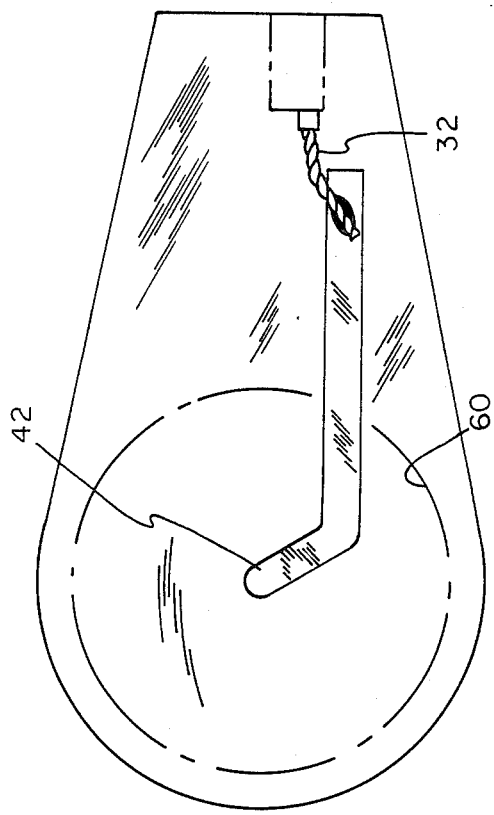
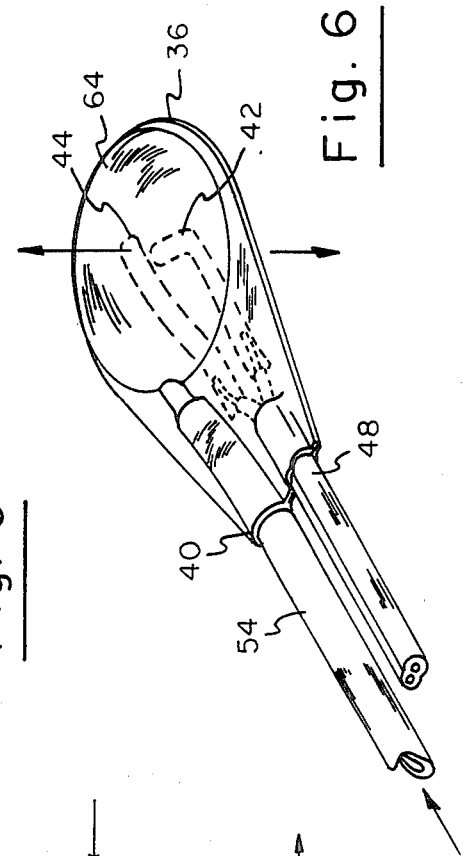
Fig. 6
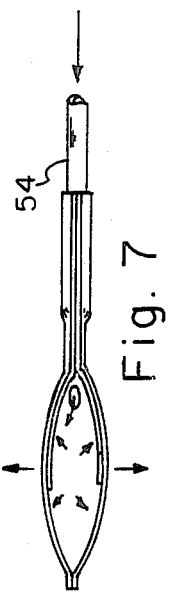
Fig. 7
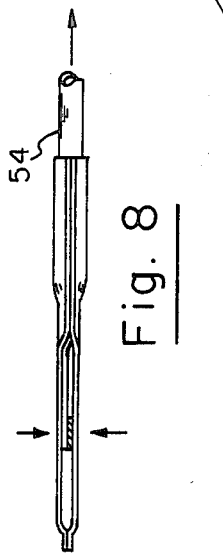
Fig. 8

INSTRUMENT FOR MEASURING PRESSURE

BACKGROUND OF THE INVENTION

When bedridden patients have to maintain a substantially motionless position on a mattress for prolonged periods of time, they develop bed sores, Decubitus Ulcers, on the skin. These sores are formed primarily because the pressure exerted on the skin surfaces under the bony prominences of the patient, which bear most of the weight of the patient when the patient's body presses against the ordinary mattress, obstructs the circulation of the blood in the body capillaries directly under these surfaces.

The present invention is directed toward a new type of portable inexpensive instrument, easily operated, which can be used to measure, quickly and accurately, the pressure exerted by any portion of the body of a bedridden individual lying on a mattress, by that section of the mattress which is engaged by this body portion.

SUMMARY OF THE INVENTION

An instrument in accordance with the principles of this invention, for measuring the pressure exerted upon a portion of the body of a bedridden invidual lying on a mattress by that section of the mattress which is engaged by this body portion includes a small flexible hollow member having a first air inlet and adapted to be positioned for use between the body portion and the section of the mattress with which the body portion is engaged.

A normally closed switch is disposed in the body with connecting leads extending out of the member. The switch is opened when the air pressure in the member is at least equal to the pressure exerted upon the body portion by the mattress section and is closed when the air pressure in the member is less than the exerted pressure.

A circuit including a lamp and a source of electric power is coupled to the connecting leads of the switch to cause the lamp to be energized and lit when the switch is closed and to cause the lamp to be deenergized and dark when the switch is open.

An air pressure meter has a second air inlet and is calibrated to display on the face of the meter air pressure readings calibrated in pressures above atmospheric pressure.

A manually operated air pump is connected to both air inlets. When the pump is actuated, it causes air to be pumped into both air inlets. This action increases the air pressure in the member. When the pressure in the member is equal to the exerted pressure, the switch is opened, the lamp is deenergized and dark, and the meter displays on its face the exerted pressure.

BRIEF DESCRIPTION OF THE DRAWINGS

FIG. 1 is a perspective view of an instrument in accordance with the invention.

FIG. 5 shows in plan both sides of a member used in the instrument and containing a switch.

FIG. 6 is a perspective view of the member of FIG. 5.

FIG. 7 is a cross sectional view of the member of FIG. 6 with the switch in open position.

FIG. 8 is a view similar to FIG. 7 but showing the switch in closed position.

DETAILED DESCRIPTION OF PREFERRED EMBODIMENTS

Figure 3:
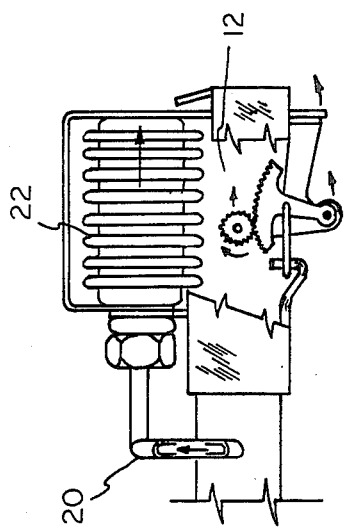
FIG. 3 is a detail view, in cross section of the air pressure meter shown in FIGS. 1 and 2.
Figure 4:
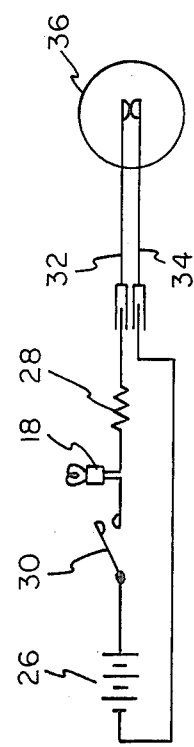
FIG. 4 is a circuit diagram of a circuit used in the instrument.
Figure 2:
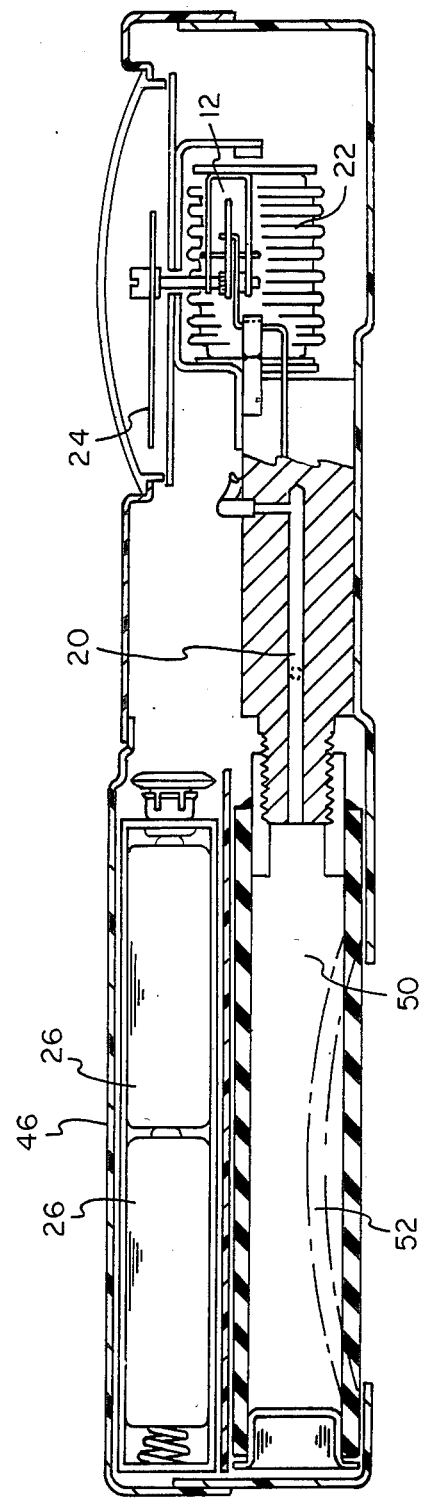
FIG. 2 is a longitudinal cross sectional view of the instrument of FIG. 1.

Referring now to FIGS. 1-8, there is shown a plastic housing with a main section 10 having an opening containing air pressure meter 12 with meter face 14 exposed. The meter face is calibrated in pounds per square inch above atmospherice pressure. The meter has an air intake channel 20 and bellows 22. The bellows is connected to the pointer 24 in known manner so that when air is forced into the channel, the bellows expands and sets the pointer on the scale of the meter face accordingly.

A red emitting electric lamp 18 is disposed removably in a socket 16. The lamp is connected in a circuit with two series connected electric cells 26, a resistor 28, a manually operated on off switch 30 and two connecting leads 32 and 34 extending into member 36. The cells are disposed in an elongated handle 46 of the housing.

Member 36 is formed from a flexible plastic and has a hollow chamber 38 with an air intake channel 40. The chamber 38 has first and second opposite walls and first and second flexible flat horizontal blade type conductors 42 and 44. Each conductor is secured to the inner surface of the corresponding wall. Normally the walls are closely spaced and the two conductors are electrically and mechanically engaged. Each conductor is connected to a corresponding one of leads 32 and 34. The conductors constitute a switch which is closed when the conductors are engaged and which is open when the conductors are separated. A flexible cable 48 is secured at one end to leads 32 and 34 in the member and at the other end to a socket in the housing whereby the circuit is electrically engaged.

A manually operated pump 50 in handle 46 is mechanically actuated by depressing and releasing diaphragm 52. The output of the pump is connected directly to channel 20 and is also connected via flexible tubing 54 to air intake channel 40 in the member 36.

In use, the member is inserted between the body portion and the section of the mattress which is engaged by the body portion. The walls of the chamber of the member are very closely spaced so that the conductors 42 and 44 are engaged. When switch 30 is closed, the lamp 18 is energized and is lit. As the pump is manually actuated, the same air pressure build up ensues in the meter and the chamber in the housing. When the pressure in the chamber is increased to be equal to the exerted pressure, the walls of the chamber become sufficiently spaced apart as to cause conductors 42 and 44 to be disengaged. The lamp is deenergized and dark and the reading of the pointer of the scale of the meter displays the magnitude of the exerted pressure.

What is claimed is:

1. An instrument for measuring the pressure exerted upon a portion of the body of a bed ridden individual lying on a mattress by that section of the mattress which is engaged by this body portion, said instrument comprising:
   a small flexible hollow member having a first air inlet and adapted to be positioned for use between the body portion and the mattress section;

a normally closed switch disposed in the member with connecting leads extending out of the member, the switch being opened when the air pressure in the member is at least equal to the pressure exerted upon the body portion by the mattress section and being closed when air pressure in the member is less than the exerted pressure;

a circuit including a lamp and an electric power source, the circuit being connected to the switch to cause the lamp to be energized and lit when the switch is closed, the lamp being deenergized and dark when the switch is open;

an air pressure meter having a meter face and a second air inlet and calibrated to display on the face air pressure readings measured in pressures above atmospheric pressure; and a manually operated air pump connected to the first and second air inlets whereby when the member is positioned for use with the switch closed and the pump is actuated, the air pressure in the member is increased until the lamp is deenergized, and the meter at the instant the lamp is deenergized displays the exerted pressure.

2. The instrument of claim 1 wherein the switch includes first and second horizontal flexible blade type conductors, one conductor overlying the other, the conductors being engaged when the switch is closed and being disengaged when the switch is open.

3. The instrument of claim 2 wherein the member is flat and flexible and has first and second closely spaced opposite walls, each conductor being secured to the inner surface of the corresponding wall, said walls being separated to an extent at which the conductors are disengaged only when the air pressure in the member is at least equal to the exerted pressure.

4. The instrument of claim 3 further including a housing for the circuit, meter and pump, the pump having a squeeze type diaphram, the circuit including at least one electric cell, the meter having an exposed face, the lamp being disposed adjacent the meter face so that the lamp and meter face are simultaneously observable.

5. The instrument of claim 4 wherein the housing has a handle and the pump and cell are disposed in the handle.

* * * * *